United States Patent [19]

Jadamec et al.

[11] Patent Number: 5,968,762
[45] Date of Patent: Oct. 19, 1999

[54] METHOD FOR DETECTING BACTERIA IN A SAMPLE

[75] Inventors: Joseph Richard Jadamec, Mystic, Conn.; Robert Bauman, Allison Park, Pa.; Carol Patricia Anderson, Mystic, Conn.; Stephen A. Jakubielski; Neslie D. Sutton, both of Uncasville, Conn.; Michael J. Kovacs, Waterford, Conn.

[73] Assignee: The University of Connecticut, Storrs, Conn.

[21] Appl. No.: 09/045,335

[22] Filed: Mar. 19, 1998

[51] Int. Cl.$^6$ ........................................................ C12Q 1/34
[52] U.S. Cl. .................................. 435/18; 435/34; 435/38
[58] Field of Search ................................ 435/18, 29, 34, 435/38, 39, 207, 252.8, 968

[56] References Cited

U.S. PATENT DOCUMENTS

| | | | |
|---|---|---|---|
| 4,242,447 | 12/1980 | Findl et al. | 435/39 |
| 4,591,554 | 5/1986 | Koumura et al. | 435/18 |
| 4,925,789 | 5/1990 | Edberg | 435/38 |
| 5,089,395 | 2/1992 | Snyder et al. | 435/39 |
| 5,236,827 | 8/1993 | Sussman et al. | 435/34 |
| 5,292,644 | 3/1994 | Berg | 435/29 |
| 5,411,867 | 5/1995 | Chang et al. | 435/18 |
| 5,429,933 | 7/1995 | Edberg | 435/34 |
| 5,443,987 | 8/1995 | DeCicco et al. | 435/4 |
| 5,510,243 | 4/1996 | Boyd et al. | 435/18 |
| 5,518,894 | 5/1996 | Berg | 435/34 |
| 5,605,812 | 2/1997 | Zomer | 435/38 |
| 5,610,029 | 3/1997 | Ehrenfeld et al. | 435/34 |
| 5,620,865 | 4/1997 | Chen et al. | 435/34 |
| 5,643,743 | 7/1997 | Chang et al. | 435/34 |
| 5,830,912 | 11/1998 | Gee et al. | 514/457 |

FOREIGN PATENT DOCUMENTS

PCT/US86/
05206 9/1986 European Pat. Off. .

*Primary Examiner*—Ralph Gitomer
*Attorney, Agent, or Firm*—Todd E. Garabedian; William A. Simons; Wiggin & Dana

[57] ABSTRACT

The invention is a method for detecting the presence of bacteria in a sample. The method of the invention utilizes the steps of (a) admixing a fluorescent conjugate with a sample to be tested for the presence of bacteria in the sample, wherein a moiety of the fluorescent conjugate is metabolized to release the fluorescent moiety of the fluorescent conjugate; (b) inducing fluorescence of the fluorescent conjugate and the fluorescent moiety of the metabolized fluorescent conjugate at 325–345 nm; (c) simultaneously detecting the fluorescence of the fluorescent conjugate at 370–380 nm and the fluorescent moiety of the metabolized fluorescent conjugate at 445–480 nm; and (d) correlating the detected fluorescence of the fluorescent conjugate and the fluorescent moiety of the metabolized fluorescent conjugate to the presence of bacteria in the sample.

18 Claims, 2 Drawing Sheets

METHOD FOR DETECTING BACTERIA IN A SAMPLE

STATEMENT OF GOVERNMENT SUPPORT

This invention was made in part with government support under grant number NA46RG0433 from the National Oceanographic and Atmospheric Administration (NOAA) and the Connecticut Sea Grant College Program. The government has certain rights in this invention.

BACKGROUND OF THE INVENTION

1. Field of the Invention

The present invention relates to a method for detecting the presence of bacteria in a sample using fluorescent conjugates. The present invention also relates to a method for detecting the presence of bacteria in a sample by measuring the fluorescent intensity ratio of a metabolized fluorescent product at a specific wavelength to the metabolizable fluorescent conjugate at a second specific wavelength.

2. Description of the Art

Bacterial contamination of products designed for human use or consumption can be a significant public health and public relations problem. Recent news reports in this country and abroad have alerted the public to the dangers of bacterial contamination. As a result, rapid methods to identify sources of bacterial contamination have become increasingly important.

The sources of bacterial contamination frequently arise from inoculation of pathogenic bacteria into water sources via intestinal excrement of animals, particularly mammals. Epidemiological studies have indicated a strong correlation between the presence of waterborne pathogenic organisms and the presence of microorganisms of mammalian intestinal origin (e.g. the bacterium *Esherichia coli*). In addition, it has been well established that the quality of products for human use or consumption is negatively impacted by the presence of pathogenic organisms. Coliform bacteria (e.g., bacteria normally present in the gut of humans or animals) in particular have been shown to correlate with outbreaks of certain diseases such as gastroenteritis, dysentery, hepatitis, and the like. These illnesses can be severe or life-threatening in children, the elderly, and immunosuppressed individuals. Bathing beaches, shellfish beds, food processing and/or handling facilities, foodstuffs (e.g., hamburger, chicken, apple cider and the like), hospital equipment, sewage treatment plants, and certain industrial lubricants are a few examples of products or locations that can become contaminated by coliform bacteria. If present in significant numbers, coliform bacteria can cause product deterioration, spoilage, disease, or serious economic loss of consumable goods. In addition, the public perception about the sanative state of a product or location can be damaged, and is difficult to repair. It is therefore important to identify those products or locations that are contaminated with coliform bacteria as quickly as possible.

To address the problem of bacterial contamination, several test methodologies have been developed. Among these are radiometric, electrochemical, chromatographic, chemiluminescent, and fluorescent methodologies.

Radiometric approaches to identifying bacterial contamination generally utilize a nutrient such as lactose or galactose that incorporates one or more radioactive atoms. Upon metabolization by the bacteria, the radiolabel becomes incorporated into the bacteria, and the bacteria can be isolated and identified by following the radiolabel. However, this method has several undesirable drawbacks. Although this method is very sensitive, it utilizes radioisotopes which can be expensive and difficult to handle. This method also generates significant quantities of radioactive waste which is difficult and expensive to dispose. In addition, testing procedures using this method generally require from about 18 to 48 hours to produce results. This time delay in identifying the source of the bacterial contamination is too great in many situations that require immediate identification.

Electrochemical, chromatographic, and chemiluminescent methods are generally less sensitive than the radiometric approaches, and therefore require higher concentrations of bacteria to generate useful data. To achieve these higher bacterial concentrations, the bacteria are frequently cultured in a growth medium for about 24 hours until enough bacteria are present for the test. Alternatively, the bacteria are concentrated using filtration or other concentrating procedures. However, these preliminary concentration steps require additional time, materials, and equipment which generally add complexity to these procedures. In addition, the total time for performing electrochemical, chromatographic, and chemiluminescent tests generally range from 24 to about 48 hours. Like the radiometric procedures, this time delay may be too great if information concerning bacterial contamination is urgently needed.

Several fluorescent methods have been described in the prior art which offer advantages over the radiometric, electrochemical, chromatographic, and chemiluminescent methods. Many of these fluorescent methods are based on the enzymatic degradation of a fluorescently labeled umbelliferone substrate with concomitant monitoring of the fluorescence at a single wavelength. The following U.S. patents are representative of the current state of the art:

U.S. Pat. No. 4,591,554 to Koumura et al. discloses a method for rapidly detecting microorganisms utilizing non-fluorescent umbelliferone derivatives such as 4-methyl-umbelliferyl-$\beta$-D-galactoside, 4-methyl umbelliferyl-$\alpha$-D-galactoside, 4-methyl umbelliferyl-phosphate, and 4-methyl umbelliferyl-pyrophosphate. Fluorescence of the liberated umbelliferone moiety is induced at 360 nm and monitored at 450 nm. High concentrations of umbelliferone derivative are used in this method ($10^{-3}$–$10^{-4}$ M).

U.S. Pat. No. 5,089,395 to Snyder et al. discloses use of a nonfluorescent umbelliferone derivative which is enzymatically converted to a fluorescent product to indicate the presence of bacteria. High concentrations of umbelliferone derivative are used in this method (about 50 $\mu$g/ml). Fluorescence of diacetylfluorescein is induced at 310 nm and monitored at 350 nm to calibrate the instrument.

U.S. Pat. No. 5,518,894 to Berg discloses a rapid method to detect the presence of coliform bacteria. However, this method uses a concentration step (filtration) in combination with incubation to increase the number of bacteria present. The fluorescence of a high concentration of hydrolyzed umbelliferone derivative is monitored as an indication of bacterial presence. Fluorescence is induced at 365 nm and monitored at 465 nm.

U.S. Pat. No. 5,429,933 to Edberg discloses detection of environmental microbes using a fluorescent metabolite and a nutrient-rich medium. No particular wavelengths to monitor fluorescence emission energy are disclosed.

U.S. Pat. No. 5,610,029 to Ehrenfeld et al. discloses a culture medium for the detection of microbes in a sample. This culture medium includes various nutrients and growth factors, as well as a fluorescent metabolite (4-methyl umbelliferyl-$\beta$-D-glucuronide). High concentrations of the fluorescent metabolite are utilized (60–90 μg/ml), and fluorescence is monitored at 366 nm.

Thus, many of the prior art methods of detecting bacteria in a sample utilize high concentrations of fluorescent metabolite, and monitor induced fluorescence at a single wavelength. However, it is well established that high concentrations of fluorescent compounds result in a quenching effect of induced fluorescence. Thus, an accurate correlation between induced fluorescence and bacterial presence is not possible using high concentrations of fluorescent metabolite. Additionally, monitoring fluorescence with a single wavelength requires instrument and temperature stability, as well as calibration of the instrument prior to each experiment. Such requirements make the analysis process time-consuming, unreliable, and highly dependent on operator skill. Accordingly, what is needed in the art is a rapid method to detect the presence of bacteria in a sample that is simple to perform, accurate, and reliable. The present invention is believed to be an answer to that need.

SUMMARY OF THE INVENTION

In one aspect, the invention is directed to a method for detecting the presence of bacteria in a sample, comprising the steps of (a) admixing a fluorescent conjugate with a sample to be tested for the presence of bacteria in the sample, wherein a portion of the fluorescent conjugate is metabolized to release the fluorescent moiety of the fluorescent conjugate; (b) inducing fluorescence of the fluorescent conjugate and the fluorescent moiety of the metabolized fluorescent conjugate at 325–345 nm; (c) detecting the fluorescence intensity of the fluorescent conjugate at 370–390 nm and the fluorescence intensity of the fluorescent moiety of the metabolized fluorescent conjugate at 445–480 nm; and (d) correlating the fluorescence intensity of the fluorescent conjugate and the fluorescence intensity of the fluorescent moiety of the metabolized fluorescent conjugate to the presence of bacteria in the sample.

In another aspect, the invention is directed to a method for detecting the presence of bacteria in a sample, comprising the steps of: (a) admixing a fluorescent conjugate selected from the group consisting of 4-methyl umbelliferyl-β-D-glucuronide, 4-methyl-umbelliferyl-β-D-galactoside, 4-methyl-umbelliferyl-N-acetyl-β-D-glucosaminidine, 4-methyl-umbelliferyl-β-D-glucoside, and combinations thereof, with a sample to be tested for the presence of bacteria in the sample, wherein the concentration of the fluorescent conjugate in the admixture is in the range from about 5–10 μg/ml and wherein a portion of the fluorescent conjugate is metabolized to release 4-methyl-umbelliferone; (b) inducing fluorescence of the fluorescent conjugate and the 4-methyl-umbelliferone at 330–340 nm; (c) detecting the fluorescence intensity of the fluorescent conjugate at 375–385 nm and the fluorescence intensity of the 4-methyl-umbelliferone at 448–455 nm; (d) calculating the ratio of the fluorescence emission intensity of the 4-methyl-umbelliferone to the fluorescence emission intensity of the fluorescent conjugate to the presence of bacteria in the sample.

These and other aspects will become apparent upon reading the following detailed description of the invention.

DESCRIPTION OF THE DRAWINGS

The invention will be more fully understood from the following detailed description taken in conjunction with the accompanying drawings in which.

DETAILED DESCRIPTION OF THE INVENTION

Figure 1:
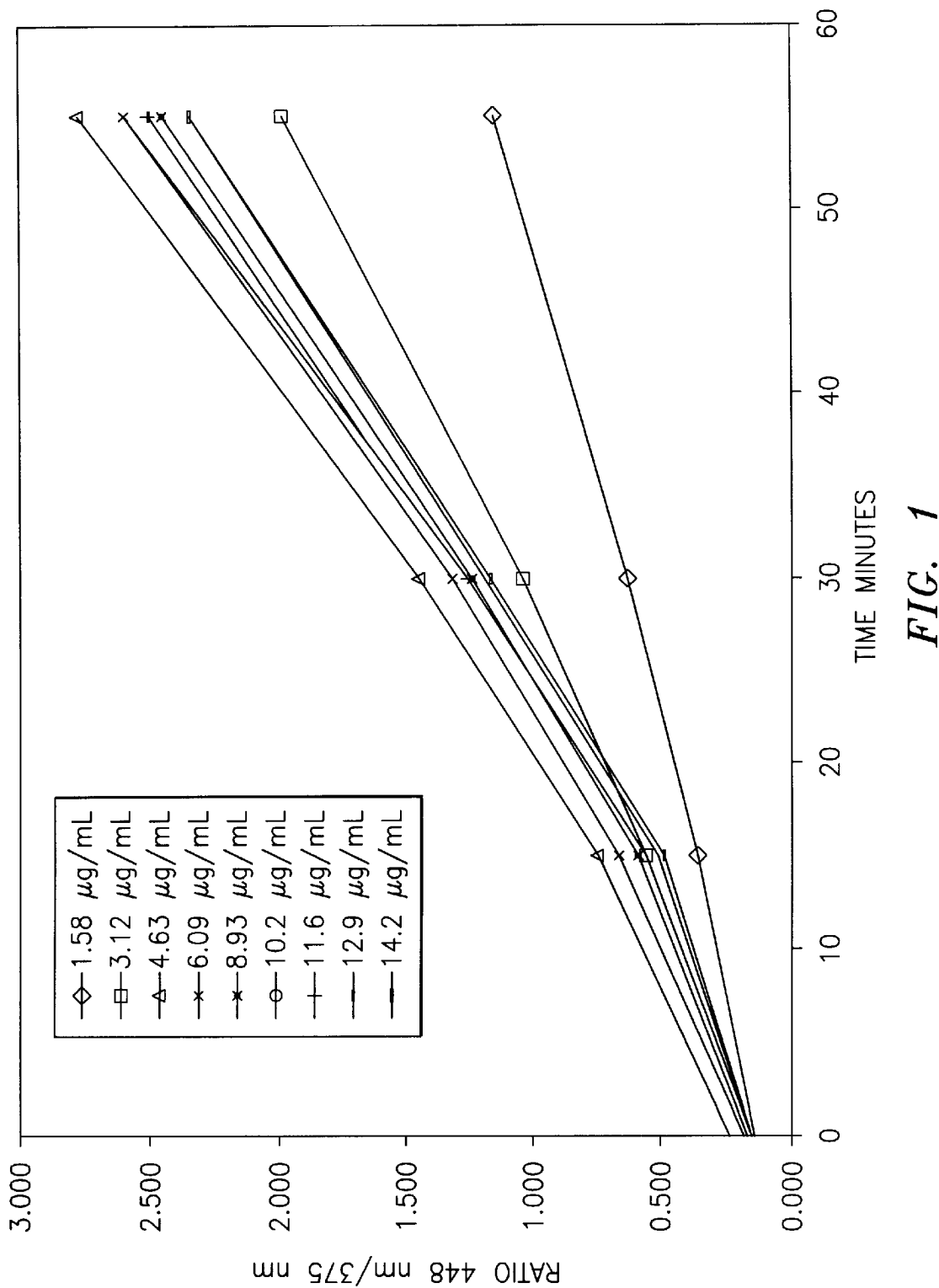
FIG. 1 is a graph showing the ratio of fluorescence intensities at 448 nm and 375 nm as a function of time for various concentrations of 4-methyl-umbelliferyl-β-D-galactoside (MUGAL)

The term "bacteria" as defined herein refers generally to single-celled prokaryotic organisms that are responsible for diseases in mammals, particularly humans. Examples of bacteria include gram-negative coliform bacteria, for example, bacteria belonging to the genus of Erwinia, Seratia, Proteus, Esherichia (e.g., Esherichia coli or E. coli) and Salmonella, or gram-positive bacteria, for example, bacteria belonging to the genus Enterococcus or Streptococcus (e.g., Streptococcus faecalis).

As defined herein, the term "fluorescent conjugate" refers to a compound comprised of a "fluorescent moiety" and a "bacterial nutrient moiety" linked together by a covalent bond that is hydrolyzable by bacterial enzymes. The fluorescent moiety of the fluorescent conjugate may be any compound that emits fluorescence upon exposure to radiation in the wavelength range from 325–345 nm. Examples of useful fluorescent moieties include umbelliferone derivatives such as 4-methyl umbelliferone (also known as 4-methyl-7-hydroxy coumarin and β-methylumbelliferone), 4-trifluoromethyl umbelliferone, 6,8-difluoro-7-hydroxy-4-methyl coumarin, 3-carboxy umbelliferone, 6-aminoquinoline, 7-amino-4-methyl coumarin, and the like. Compounds having longer excitation wavelengths, such as fluorescein and resorufin which have excitation wavelengths in the 400 nm range, may also be used according to the method of the invention. The "bacterial nutrient moiety" of the fluorescent conjugate may be any nutrient suitable for bacterial consumption, such as glucoside, glucuronide, galactoside, glucosaminidine, and the like. Generally, certain nutrient moieties are preferred by different species of bacteria. For example, glucuronide is preferred by E. coli; glucosaminide is preferred by S. faecalis; and glucoside is preferred by Enterococci. Galactoside is a preferred nutrient by several species of bacteria and is therefore useful to detect many species of bacteria, for example total coliform bacteria. Thus, it is possible to detect particular species of bacteria by proper selection of a nutrient. Additionally, combinations of fluorescent conjugates having different nutrient moieties allows one to detect multiple bacteria species at one time according to the method of the invention.

The term "fluorescence emission intensity" as defined herein refers to the value of the measured fluorescence emission spectrum in arbitrary units.

Examples of fluorescent conjugates that are useful in the method of the invention are 4-methyl umbelliferyl-β-D-glucuronide (MUG), 4-trifluoromethylumbelliferyl-β-D-glucuronide (TFMUG), 4-methyl-umbelliferyl-β-D-galactoside (MUGAL), 4-methyl-umbelliferyl-N-acetyl-β-D-glucosaminidine (MEG); and 4-methyl-umbelliferyl-β-D-glucoside (MEGUL). A particularly useful fluorescent conjugate is 4-methyl-umbelliferyl-β-D-galactoside. Table 1 shows these useful fluorescent conjugates, their target bacteria, and their emission wavelengths. In Table 1, $\lambda_1$ and $\lambda_2$ are both emission wavelengths.

TABLE 1

Data for Fluorescent Selected Fluorescent Conjugates

| Fluorescent conjugate | Target Bacteria | $\lambda_1$ (nm) | $\lambda_2$ (nm) |
|---|---|---|---|
| 4-methyl umbelliferyl-β-D-glucuronide (MUG) | E. coli | 380 | 450 |
| 4-trifluoromethylumbelliferyl-β-D-glucuronide (TFMUG) | E. coli | 410 | 500 |
| 4-methyl-umbelliferyl-β-D-galactoside (MUGAL) | Total coliform | 380 | 450 |
| 4-methyl-umbelliferyl-N-acetyl-β-D-glucosaminidine (MEG) | S. faecalis | 380 | 450 |
| 4-methyl-umbelliferyl-β-D-glucoside (MEGUL) | Enterococci | 380 | 450 |

According to the method of the invention, the fluorescent conjugate is first added to a sample suspected of being contaminated with bacteria. The sample may be from any source (e.g., liquid, solid, or vapor). Samples in which it is particularly important to know if bacterial contamination exists include bathing beach water, shellfish bed water, food processing and/or handling equipment, perishable foodstuffs such as hamburger, turkey, chicken, eggs, apple cider and the like, hospital or restaurant equipment, sewage treatment plant equipment, and industrial lubricants which are potential growth media for several species of bacteria.

The sample may be either liquid (e.g., bathing beach water or shellfish bed water) or solid (e.g., hamburger, chicken, etc.). Liquid samples are preferred in order to facilitate rapid and accurate fluorescent measurements. In the case of a solid sample such as a foodstuff, a moiety of the solid material may be used to inoculate a saline solution or an appropriate buffering medium such as phosphate, HEPES (N-(2-hydroxyethyl)piperazine-N'-(2-ethane sulfonic acid), PIPES (1,4-piperazine bis(ethanesulfonic acid), or other suitable buffer. Contaminated equipment may be wiped with a sterile swab or cloth to transfer bacteria to the buffering medium, growth medium or saline solution. Bacteria in samples to be tested according to the method of the invention may be concentrated by conventional means such as filtration to increase bacterial population and fluorescence response if desired.

Additional additives such as growth inducers or nutrients may be added to the sample in order to encourage bacterial growth and thereby enhance the intensity of the fluorescent signal. Examples of additional additives include lytic agents such as toluene or chloroform, lytic enzymes, vitamins, minerals, antibiotics (e.g., vancomycin, colistin, ansiomycin, monensin, nalidixic acid and the like), pyruvate salts, detergents, surfactants, bile salts, and the like. Preferably, additional additives are present in the admixture in the nanomolar ($10^{-9}$ M) to micromolar ($10^{-6}$ M) range.

The final concentration of fluorescent conjugate added to the sample is preferably in the range from about 2 to 20 μg/ml, more preferably in the range from about 5 to 15 μg/ml, and most preferably from about 5–10 μg/ml. Generally, lower concentrations of fluorescent conjugate are preferred to minimize fluorescence quenching commonly observed at higher concentrations of fluorescent conjugate. At high concentrations of fluorescent conjugate (e.g., greater than about 25 μg/ml), the fluorescent response is no longer a linear correlation due to quenching effects and results in skewed measurement data.

A preferable temperature range for practicing the method of the invention is room temperature (15–25° C.) to about 45° C., and more preferably 35–45° C.

Upon exposure to a sample that contains bacteria, a moiety of the fluorescent conjugate is hydrolyzed by bacterial enzymes present in the medium to separate the fluorescent moiety and the nutrient moiety. The fluorescent conjugate and the released fluorescent moiety may then be simultaneously detected by appropriate instrumentation to confirm the presence of bacteria in the sample. Thus, upon addition of the fluorescent conjugate to the contaminated sample, virtually all of the fluorescence in the sample is derived from the fluorescent conjugate alone. After a short period of time (generally from about 30 seconds to 5 minutes), a moiety of the fluorescent conjugate is metabolized to its constituent parts, namely, the fluorescent moiety and the bacterial nutrient moiety. Since the fluorescent moiety has a fluorescent spectrum that is distinguishable from that of the fluorescent conjugate, it is possible to monitor the metabolization rate of the fluorescent conjugate and the concomitant generation of the fluorescent moiety simultaneously as an indication of bacterial presence by monitoring their individual fluorescent emission wavelengths. In other words, if bacteria are present in the sample, the concentration (and therefore the fluorescence intensity) of the fluorescent conjugate should decrease over time, while the concentration and fluorescence intensity of the fluorescent moiety liberated from the metabolized fluorescent conjugate should increase over time.

Following addition of fluorescent conjugate to the sample, metabolization of the fluorescent conjugate takes place immediately if bacteria are present. Incubation times after the fluorescent conjugate is added to the sample to be tested can range from instantaneous to several hours depending on the amount of bacteria in the sample. Generally, lower levels of bacteria in a sample require longer incubation times or concentration to increase the initial bacteria population. Useful incubation times range from 2 minutes to about 2 hours. Thus, the method of the invention can rapidly determine whether a sample is contaminated with bacteria.

As shown in Table 2, the fluorescent conjugates MUG and MUGAL have fluorescent excitation wavelengths that are similar to the excitation wavelength of the fluorescent moiety 4-methylumbelliferone. However, the fluorescence emission wavelengths of these compounds are different and allow detection of each molecule individually by its unique fluorescence emission spectrum.

TABLE 2

Fluorescence Spectra of Selected Umbelliferone Derivatives

| Compound | Fluorescence Excitation Wavelength (nm) | Fluorescence Emission Wavelength (nm) |
|---|---|---|
| MUG | 319–345 | 373–377 |
| MUGAL | 320–344 | 374–375 |
| 4-methylumbelliferone | 327–353 | 448–450 |

Excitation wavelengths that are useful according to the method of the invention are preferably from about 325 nm to about 345 nm, and more preferably from about 330 to about 340 nm. Preferable wavelengths to monitor the intensity of the fluorescence emission of the fluorescent conjugate range from 370–390 nm, more preferably 375–385 nm, and most preferably 380 nm. Preferable wavelengths to monitor the intensity of the fluorescence emission of the fluorescent moiety range from 448–480 nm, more preferably 448–455 nm, and most preferably 450 nm. Generally, the emission and excitation maximum wavelength for any particular combination of fluorescent conjugate and fluorescent moiety depends on the concentration of those molecules in the sample. Choice of a particular wavelength is within the skill of the ordinary skilled practitioner and can be established without undue experimentation.

The fluorescence can be monitored by any method known in the art. Suitable laboratory apparatus to induce and detect fluorescence are available commercially from Perkin Elmer, Farrand Optical, and Optical Technology Devices Inc. Alternatively, portable devices may be utilized to assess fluorescence and accompanying bacterial contamination "on-site" (e.g., the 10-AU digital field fluorometer available from Turner Inc.).

As described above, monitoring single fluorescence emission wavelengths generally requires instrument and temperature stability, as well as calibration of the instrument prior to each experiment. Variations in sample cuvettes or vials can also affect the fluorescence measurements. In order to compensate for these variables, the method of the invention employs a correlation between the fluorescence measurements of the fluorescent conjugate and the fluorescence measurements of the fluorescent moiety. As defined herein, the term "correlating" refers to an evaluation of the ratio of the fluorescence intensity of the fluorescent moiety ($F_m$) to the fluorescence intensity of the fluorescent conjugate ($F_c$):

$F_m/F_c$

The ratio of the fluorescence intensity of the fluorescent moiety to the fluorescence intensity of the fluorescent conjugate as described above allows the operator to determine the presence or absence of specific bacteria in the sample, and to determine the amount of bacteria present in the sample based on the magnitude of the ratio. In addition, the correlation step according to the method of the invention compensates for many variables such as instrument source, flaws or variations in sample vials, light transmission properties of the sample, background absorbance of the sample, detector instability, temperature, differential sample handling and operator skill, and the like. Thus, these factors, which can cause large variations in the measured fluorescence when a single wavelength is used, become insignificant in the calculated ratio data according to the method of the invention.

FIG. 1 shows a series of fluorescence response curves that depict the ratio of fluorescence intensities at 448 nm and 375 nm as a function of time for various concentrations of 4-methyl-umbelliferyl-β-D-galactoside (MUGAL) and a constant amount of bacteria. As shown in FIG. 1, the ratio of the fluorescence intensities at 448 and 375 nm increases over time, and the rate the ratio changes over time depends on the concentration of fluorescent conjugate in the sample increases up to about 5 μg/ml. FIG. 1 illustrates that there is an optimum level of substrate for bacteria growth and that increasing the amount of substrate does not significantly increase the calculated fluorescence ratio over time.

EXAMPLES AND COMPARISON EXAMPLE

The present invention is further described in detail by means of the following examples and comparison example. However, this invention is not intended to be limited by these examples and comparisons. All parts and percentages are shown by weight:volume, and all temperatures are in degrees Celsius, unless explicitly stated otherwise.

EXAMPLE 1

Detection of E. coli bacteria was undertaken using 4-methylumbelliferyl-β-D-glucuronide (MUG) as the fluorescent conjugate. The experiment was conducted at room temperature and no other nutrient source was added to the reaction mixture.

An E. coli culture was prepared from Bactrol™ disks ATCC 25922 (available from DIFCO) in tryptic soy broth and incubated at 35° C. until the culture reached a stationary growth phase. The E. coli culture was removed from the incubator and four dilutions of the culture were prepared as follows. A 0.5 mL aliquot of E. coli culture was removed and diluted to a final volume of 50 mL in a sterile tube using a 0.85% saline solution (Sample A). Sample A was then vortexed for 1 minute and a 5 mL portion was removed and diluted to a final volume of 50 mL in a sterile tube using a 0.85% saline solution (Sample B). Sample B was then vortexed for 1 minute and a 5 mL portion was removed and diluted to a final volume of 50 mL in a sterile tube using a 0.85% saline solution (Sample C). Sample C was then vortexed for 1 minute and a 5 mL portion was removed and diluted to a final volume of 50 mL in a sterile tube using a 0.85% saline solution (Sample D).

All samples and a blank (0.85% aqueous saline) were prepared as follows. A 3.8 mL aliquot of each sample and blank was placed into separate 4 mL glass vial (15 mm outside diameter, 45 mm in height) with threaded cap (Fisher Scientific Company). The vial cap has a Teflon fluorocarbon liner. All subsequent fluorescence measurements were made in these glass vials.

The blank sample was inoculated first with 0.225 mL aqueous solution of MUG (Sigma Chemical Co., St. Louis, Mo.). The concentration of MUG in the blank sample was 5.7 μg/mL. After addition of MUG to the blank sample, the fluorescence emission intensity at 380 nm and 450 nm of the blank sample was measured at room temperature (18° C.) at thirty minute intervals for 2.5 hours. The same procedure was repeated for Samples A, B, C, and D.

All fluorescence measurements were made using a Perkin Elmer MPF-66 Fluorescence Spectrometer in the uncorrected mode. The excitation wavelength used in this experiment was 334 nm. The excitation and emission slit widths were 4.0 and 10.0 nm respectively. The ratio of the 450 nm intensity to the 380 nm intensity was calculated and recorded.

Quantitation of viable E coli contained in the 50 mL tubes containing Samples A, B, C, and D was determined by the spread plate technique. 0.1 mL volumes of Samples A, B, C, and D, and decimal dilution of these samples in sterile saline (0.85%), were pipetted onto the surface of petri dishes containing MacConkey's agar. Prior to withdrawing the 0.1 mL sample(s) from each sample 50 mL tube, the tubes were vortexed for one minute to obtain a homogeneous solution. Plates were placed on specially designed turntables and the 0.1 mL volumes were distributed evenly over the agar surfaces using sterile (alcohol-flamed) glass rods until the liquid was totally absorbed into the agar. Plates were incubated at 35–37° C. overnight and typical E. coli colonies (dark red surrounded by a zone of precipitated dye) were counted using an illuminated colony counter. Number of colonies per plate times the reciprocal of the dilution yielded the reported plate count colony-forming units (cfus) per mL of sample. Plates with between 30 and 300 colonies were considered countable and those in this range were averaged for the reported cfus/mL of the Samples A, B, C, and D contained in the 50 mL tubes.

Figure 2:
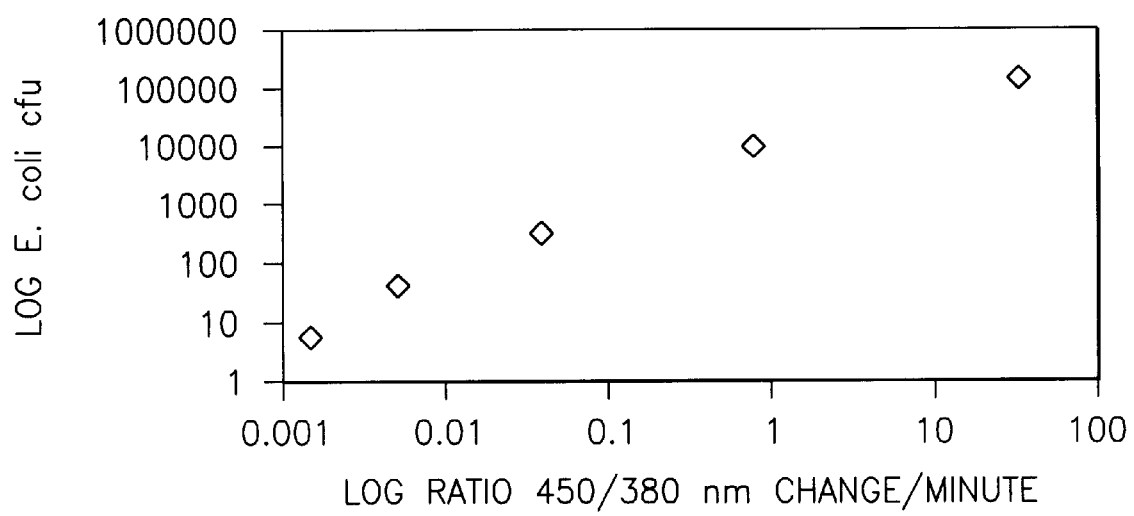
FIG. 2 is a graph showing 4-methyl umbelliferyl-β-D-glucuronide (MUG) substrate ratio correlation with E. coli colony forming units (cfus) at room temperature.

The data are shown in Table 3 (for data up to 2.5 hours) and FIG. 2 (for data up to 19.5 hours).

TABLE 3

Data for Example 1 (2.5 Hours)

| Bacteria concentration (cfu/ml) | Detection Time (minutes) | ΔR × 100 per min. |
|---|---|---|
| 120,000 | <1 | 218.36 |
| 8,400 | <3 | 34.62 |
| 310 | <80 | 2.01 |

As illustrated in Table 3 and FIG. 2, as detection time increases, the amount of bacteria detected (expressed as ΔR×100 per minute) increases and correlates well with the increasing amount of bacteria quantified by the spread plate method.

EXAMPLE 2

This experiment shows the utility of the ratio method of the present invention relative to the single wavelength fluorescence monitoring of the prior art for aqueous samples containing leachable/soluble organic matter rendering the analyzed solutions colored, i.e. amber to brown in color.

A sample of compost (composed of vegetable scraps, coffee grinds, paper, citrus, meat, bread, and wood scraps) was provided by the Connecticut Department of Environmental Protection Recycling Program. The compost sample had previously been analyzed by the Connecticut Department of Public Health (DPH). The DPH prepared the solid compost sample for analysis by column elution techniques. The DPH reported that the liquid elutriate was found to contain >160,000/100 mL total coliform bacteria using the most probable number method (MPN).

This sample was analyzed by the ratio method in which the fluorescence emission intensity of the fluorogenic substrate MUGAL (4-methylumbelliferyl-β-D-Galactoside) and the released fluorophore 4-methylumbelliferone (4-methyl 7-hydroxy coumarin) were monitored, and by single wavelength techniques in which only the released fluorophore 4-methylumbelliferone (4-methyl 7-hydroxy coumarin) was monitored. The MUGAL substrate used in this study was obtained from SIGMA (St. Louis, Mo.).

A five gram sample of compost was placed in 100 mL of a 0.85% saline solution contained in a 125 mL separatory funnel. The compost/saline mixture was then shaken by hand for five minutes and allowed to stand overnight at room temperature. Three unfiltered aliquots of the aqueous fraction, contained in the separatory funnel were removed using a glass pipette and prepared for analysis. The separatory funnel was not disturbed during the withdrawal of these three aliquots, i.e., no attempt was made to ensure that a homogenous distribution of bacteria was present when each aliquot was removed.

Three samples were prepared for analysis by diluting each compost elutriate aliquot with 0.85% aqueous saline to a final volume of 4.0 mL. The sample dilutions were 3.8 mL elutriate to 4.0 mL (Sample A), 1.9 mL elutriate to 4.0 mL (Sample B), and 1.0 mL elutriate to 4.0 mL (Sample C). MUGAL was added to each sample to a final concentration of 5.4 μg/mL. The blank used in this experiment was 0.85% saline having a MUGAL concentration of 5.4 μg/mL. All fluorescence measurements were made in standard capped glass sample vials having a 15 mm OD and a 45 mm vertical height. The vial cap has a Teflon fluorocarbon liner.

After addition of MUGAL to the blank sample, the fluorescence emission intensity at 380 nm and 450 nm was measured at room temperature (18° C.) using a Perkin Elmer MPF-66 Fluorescence Spectrometer and a fluorescence excitation wavelength of 334 nm with excitation and emission slit widths of 4.0 and 10.0 nm respectively. Following the fluorescence measurement, the blank was immediately placed into a Sybron Thermolyne Dri-Bath block incubator (Model DB 17615) maintained at a temperature of 35–36° C. The same procedure was repeated for Samples A, B and C.

After 30 minutes of incubation at 35–36° C., the samples were removed from the incubator one at a time, and the fluorescence emission intensity at 380 and 450 nm was measured for each sample. The samples were then left at room temperature (18° C.) for approximately 15–16 minutes to study the effect of temperature variations on the fluorescence emission intensity of the blank and samples at 380 and 450 nm. Two additional measurements of each sample was made at 6 and 12 minutes prior to returning all samples to the incubator. After 15–16 minutes the samples were removed and the same set of measurements were repeated. The samples were then incubated for a third 15–16 minute period and removed for analysis in the same manner as the previous two sequences. Total elapsed time over which measurements were made from initial inoculation of the blank and samples to the final set of measurements was 136 minutes. The data obtained in this experiment is show in Table 4 (single wavelength monitoring at 450 nm) and Table 5 (dual wavelength monitoring and calculated ratios of 380 nm to 450 nm).

The initial readings of each sample measured at room temperature were used as blank corrections for readings after the three incubations times, and as such are indicated as zero.

TABLE 4

| Relative Fluorescence Intensity (arbitrary units) at 450 nm | | | | |
|---|---|---|---|---|
| TIME (min) Initial (t = 0) | 45 | 92 | 136 | ΔF per min. |
| Blank 561 | 450 | 459 | 473 | — |
| Sample A 0 | 44 | 100 | 152 | 1.12 |
| Sample B 0 | 252 | 607 | 937 | 6.89 |
| Sample C 0 | 501 | 1225 | 1932 | 14.2 |

TABLE 5

| Dual Wavelength Monitoring at 450 nm and 380 nm Expressed as Ratio 450/380 | | | | |
|---|---|---|---|---|
| TIME (min.) Initial (t = 0) | 45 | 92 | 136 | ΔR × 100 per minute |
| Blank 0.076 | 0.082 | 0.083 | 0.084 | — |
| Sample A 0 | 4.05 | 8.51 | 13.1 | 9.63 |
| Sample B 0 | 1.34 | 2.88 | 4.44 | 3.26 |
| Sample C 0 | 0.658 | 1.40 | 2.17 | 1.60 |

This same experiment was repeated three times and the results obtained were similar. The data shown in Table 4 indicate that the sample having the lowest level of bacterial present (Sample C) has the highest intensity readings and the greatest change in relative fluorescence intensity (ΔF) per minute. This result is contrary to the dilution scheme described above. According to the dilution scheme described above, the relative concentration of bacteria present in Sample C should be significantly less than that of Sample A. This extraordinary result illustrates the effect of sample matrix properties (e.g., transmission properties of the sample, background absorbance of the sample, etc.) on fluorescence emission measurements made at a single wavelength.

In contrast, as shown in Table 5, the ratio method of the present invention compensates for sample matrix effects and the change in ratio per minute (ΔR) as well as the magnitude of the ratios at any monitoring time, relative to each other, indicate that the three samples contain varying amount of bacteria and that Sample A contains significantly more bacteria than Sample C.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entirety.

What is claimed is:

1. A method for detecting the presence of bacteria in a sample, comprising the steps of:
   (a) forming an admixture comprising a fluorescent conjugate and a sample to be tested for the presence of bacteria in said sample, said fluorescent conjugate comprising a fluorescent moiety and a bacterial nutrient moiety linked together by a covalent bond that is hydrolyzable by bacterial enzymes, wherein a portion of said fluorescent conjugate is metabolized by bacterial enzymes in said sample to produce a released fluorescent moiety;
   (b) inducing a fluorescence emission of said fluorescent conjugate and a fluorescence emission of said released fluorescent moiety at 325–345 nm;
   (c) detecting the induced fluorescence emission of said fluorescent conjugate at 370–390 nm and the induced fluorescence emission of said released fluorescent moiety at 445–480 nm;
   (d) calculating a ratio of said fluorescence emission of said released fluorescent moiety to said fluorescence emission of said fluorescent conjugate; and
   (e) correlating said ratio to the presence of bacteria in the sample.

2. The method of claim 1, wherein said fluorescent conjugate is selected from the group consisting of 4-methyl umbelliferyl-β-D-glucuronide, 4-trifluoromethylumbelliferyl-β-D-glucuronide, 4-methyl-umbelliferyl-β-D-galactoside, 4-methyl-umbelliferyl-N-acetyl-β-D-glucosaminidine, 4-methyl-umbelliferyl-β-D-glucoside, and combinations thereof.

3. The method of claim 1, wherein said fluorescent moiety is selected from the group consisting of 4-methyl umbelliferone, 4-trifluoromethyl umbelliferone, 6,8-difluoro-7-hydroxy-4-methyl coumarin, 3-carboxy umbelliferone, 6-amino-quinoline, 7-amino-4-methyl coumarin, and combinations thereof.

4. The method of claim 1, wherein said fluorescent conjugate has a concentration in said admixture in the range from 2 to 20 μg/ml.

5. The method of claim 4, wherein said fluorescent conjugate has a concentration in said admixture in the range from 5 to 15 μg/ml.

6. The method of claim 5, wherein said fluorescent conjugate has a concentration in said admixture in the range from about 5–10 μg/ml.

7. The method of claim 1, wherein said fluorescence emission of said fluorescent conjugate and said fluorescent emission of said fluorescent moiety are induced in the range of 330–340 nm.

8. The method of claim 1, wherein said fluorescent emission of said fluorescent conjugate is measured at 375–385 nm and said fluorescence emission of said fluorescent moiety of said metabolized fluorescent conjugate is measured at 448–455 nm.

9. The method of claim 1, wherein the temperature of said method ranges from about 15° C. to about 45° C.

10. The method of claim 1, wherein said bacteria are coliform bacteria.

11. The method of claim 10, wherein said coliform bacteria are selected from the group consisting of Esherichia, Erwinia, Seratia, Proteus, Salmonella, and combinations thereof.

12. The method of claim 1, wherein said admixture further comprises additional additives selected from the group consisting of growth inducers, nutrients, toluene, chloroform, lytic enzymes, vitamins, minerals, antibiotics, pyruvate salts, detergents, surfactants, bile salts, and combinations thereof.

13. The method of claim 12, wherein said additional additives are present in said admixture in the nanomolar ($10^{-9}$M) to micromolar ($10^{-6}$M) range.

14. A method for detecting the presence of bacteria in a sample, comprising the steps of:
   (a) forming an admixture comprising a fluorescent conjugate selected from the group consisting of 4-methyl umbelliferyl-β-D-glucuronide, 4-methyl-umbelliferyl-β-D-galactoside, 4-methyl-umbelliferyl-N-acetyl-β-D-glucosaminidine, 4-methyl-umbelliferyl-β-D-glucoside, and combinations thereof, with a sample to be tested for the presence of bacteria in said sample, wherein said fluorescent conjugate in said admixture has a concentration in the range from about 5–10 μg/ml and wherein a portion of said fluorescent conjugate is metabolized by bacterial enzymes in said sample to release 4-methyl-umbelliferone;
   (b) inducing a fluorescence emission of said fluorescent conjugate and a fluorescence emission of said 4-methyl-umbelliferone at 330–340 nm;
   (c) detecting the induced fluorescence emission of said fluorescent conjugate at 375–385 nm and the induced fluorescence emission of said 4-methyl-umbelliferone at 448–455 nm;
   (d) calculating the ratio of the fluorescence emission of said 4-methyl-umbelliferone to the fluorescence emission of said fluorescent conjugate and
   (e) correlating said ratio to the presence of bacteria in the sample.

15. The method of claim 14, wherein the temperature of said method ranges from about 15° C. to about 45° C.

16. The method of claim 14, wherein said bacteria are coliform bacteria selected from the group consisting of Esherichia, Erwinia, Seratia, Proteus, Salmonella, and combinations thereof.

17. The method of claim 14, wherein said admixture further comprises additional additives selected from the group consisting of growth inducers, nutrients, toluene, chloroform, lytic enzymes, vitamins, minerals, antibiotics, pyruvate salts, detergents, surfactants, bile salts, and combinations thereof.

18. The method of claim 17, wherein said additional additives are present in said admixture in the nanomolar ($10^{-9}$M) to micromolar ($10^{-6}$M) range.

* * * * *